(12) United States Patent
Seidel et al.

(10) Patent No.: US 7,019,056 B2
(45) Date of Patent: *Mar. 28, 2006

(54) FLAME RETARDANTS WHICH CONTAIN PHOSPHORUS, AND FLAME-RETARDANT THERMOPLASTIC MOLDING COMPOSITIONS

(75) Inventors: Andreas Seidel, Dormagen (DE); Käthe Baumann, Wuppertal (DE); Thomas Eckel, Dormagen (DE); Michael Zobel, Köln (DE); Jörn Stölting, Köln (DE); Dieter Wittmann, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/039,266

(22) Filed: Jan. 4, 2002

(65) Prior Publication Data

US 2002/0137821 A1    Sep. 26, 2002

(30) Foreign Application Priority Data

Jan. 9, 2001 (DE) ................................ 101 00 591

(51) Int. Cl.
   *C08K 5/523* (2006.01)
(52) U.S. Cl. ........................ 524/127; 524/451; 558/162
(58) Field of Classification Search ........ 524/126–127, 524/451; 558/167
   See application file for complete search history.

(56) References Cited

U.S. PATENT DOCUMENTS

| | | | |
|---|---|---|---|
| 5,061,745 A | 10/1991 | Wittmann et al. | 524/139 |
| 5,183,905 A | 2/1993 | Aaronson et al. | 549/218 |
| 5,455,292 A | 10/1995 | Kakegawa et al. | 524/141 |
| 5,672,645 A | 9/1997 | Eckel et al. | 524/127 |
| RE36,902 E | 10/2000 | Eckel et al. | 524/127 |
| 6,569,930 B1 * | 5/2003 | Eckel et al. | 524/127 |
| 6,596,794 B1 * | 7/2003 | Eckel et al. | 524/123 |

FOREIGN PATENT DOCUMENTS

| | | |
|---|---|---|
| EP | 0 501 582 A1 | 9/1992 |
| EP | 0 363 608 | 1/1994 |
| EP | 0 672 717 | 9/1995 |
| EP | 0 816 434 | 1/1998 |
| WO | 99/07779 | 2/1999 |
| WO | WO 99/07782 * | 2/1999 |
| WO | WO00/31173 * | 6/2000 |
| WO | 00/77012 A1 | 12/2000 |
| WO | 01/34683 A1 | 5/2001 |

OTHER PUBLICATIONS

Chemical Abstracts, vol. 97, No. 16, Oct. 18, 1982 Columbus, Ohio, US; abstract No. 128624, Adeka Argus Chemical Co., Ltd., Japan: "Weather-resistant halopolymers" XP002193237 (dieses Dokument wurde zitiert, da es als englische Zusammenfassung des oben angeführten japanischen Dokumentes anzusehen est) Zusammenfassung & JP 57 055947 A (Adeka Argus Chemical Co., Ltd., Japan) Apr. 3, 1982.

* cited by examiner

*Primary Examiner*—Peter Szekely
(74) *Attorney, Agent, or Firm*—Joseph C. Gil; Aron Preis

(57) ABSTRACT

An oligophosphate of general formula

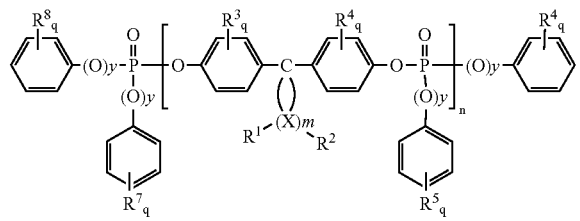

is disclosed. The oligophosphate is suitable as a flame retardant for thermoplastic molding compositions that exhibit a good flame-retardant effect, improved dimensional stability under the effect of heat, a good level of toughness and excellent flowability.

9 Claims, No Drawings

FLAME RETARDANTS WHICH CONTAIN PHOSPHORUS, AND FLAME-RETARDANT THERMOPLASTIC MOLDING COMPOSITIONS

FIELD OF THE INVENTION

This invention relates to new oligophosphates which act as flame retardants, and to thermoplastic compositions (molding compositions) which contain these flame retardants.

SUMMARY OF THE INVENTION

An oligophosphate conforming to a particular structural formula is disclosed. The oligophosphate is suitable as a flame retardant for thermoplastic molding compositions that exhibit a good flame-retardant effect, improved dimensional stability under the effect of heat, a good level of toughness and excellent flowability.

BACKGROUND OF THE INVENTION

Flame-retardant, impact-resistant modified polycarbonate molding compositions are known. Compounds which contain phosphorus, particularly aromatic esters of phosphoric acid, are often used as flame retardants on a large industrial scale.

U.S. Pat. No. 5,061,745 describes polymer mixtures comprising aromatic polycarbonates, ABS graft polymers and/or styrene-containing copolymers and esters of monophosphoric acid as flame retardant additives. One disadvantage of esters of monophosphoric acid is their plasticizing effect, which results in a considerable decrease in the dimensional stability of these polymers under the effect of heat. Moreover, for many applications these compounds are too volatile and exhibit too great a capacity for migration in the polymer composition, which under unfavorable injection molding conditions may result in the bleeding out of the flame-retardant additive and in unwanted contamination of the surfaces of the injection mold, which is termed a "juicing phenomenon".

Said juicing phenomenon may be very substantially suppressed, and the dimensional stability under the effect of heat of the material may easily be increased, by the use of oligomers of esters of phosphoric acid or mixtures of oligo- and monophosphoric acid esters as flame retardants in PC/ABS-molding compositions, as described in EP-A 0 363 608 and EP-A 0 640 655. For many applications, however, the dimensional stability under the effect of heat which is thereby obtained is still unsatisfactory.

WO 99/07779 describes the use of oligophosphates based on bi-phenylene dihydroxide as flame retardants in PC/ABS molding compositions. These phosphates exert a significantly reduced plasticiser effect on the polymer composition, so that a greater dimensional stability under the effect of heat may be achieved. However, molding compositions which are provided with this additive exhibit poor flowability, which in many cases is not satisfactory for the processing of the material by injection molding.

Other esters of oligophosphoric acid and the use thereof as flame retardants in PC/ABS molding compositions are described in EP-A 0 816 434 (oligophosphates based on bisphenol S), EP-A 0 672 717 (alkyl-substituted oligophosphates of the p-hydroquinone type), U.S. Pat. No. 5,455,292 (alkyl-substituted oligophosphates based on bisphenol A), U.S. Pat. No. 5,864,004 (oligophosphates based on bisphenol A) and U.S. Pat. No. 5,183,905 (oligophosphates based on phenolphthalein). PC/ABS molding compositions which are made flame-retardant with these compounds do in fact exhibit dimensional stability under the effect of heat which is improved compared with that achieved with conventional flame retardants, but for many applications still do not exhibit sufficient dimensional stability under the effect of heat or exhibit deficiencies in flowability or toughness.

DETAILED DESCRIPTION OF THE INVENTION

Consequently, the underlying object of the present invention is to provide PC/ABS molding compositions which exhibit improved dimensional stability under the effect of heat whilst still exhibiting a good level of toughness and excellent flowability.

This object is achieved by a new compound, which contains phosphorus, of general formula

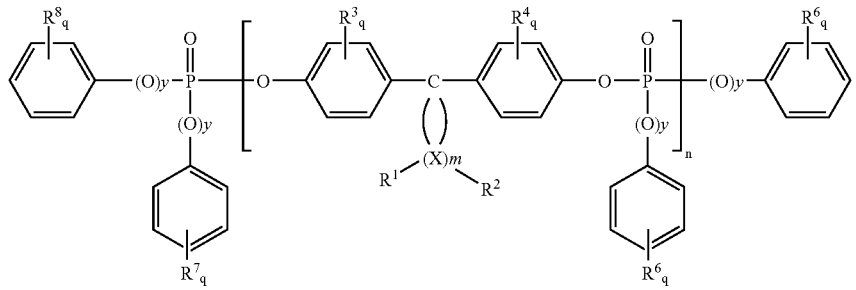

which exhibits a flame retardant effect, wherein $R^1$ and $R^2$ are selected individually and independently of each other for each X, and denote hydrogen, a halogen, an alkyl which is unsubstituted or substituted with a halogen, a cycloalkyl or an aryl, each containing 1 to 20 carbon atoms preferably containing 1 to 10 carbon atoms, or $R^1$ and $R^2$, together with the carbon atom X to which they are bonded, form the structure

or a cycloalkyl structure which is unsubstituted or substituted with a halogen, $R^3$ to $R^8$, independently of each other denote an alkyl comprising 1 to 10 carbon atoms or a halogen, X denotes carbon, m denotes an integer of 4 to 7, preferably 4 or 5, n denotes an integer of 1 to 30, preferred 1 to 15, particularly 1 to 5, y is 0 or 1, preferably 1, and q independent of each other represent integers of 0 to 5.

$R^1$ or $R^2$ on a carbon atom X, together with a corresponding $R^{1'}$ or $R^{2'}$ on a different carbon atom X, may also form a cyclic structure, for example a cycloalkyl or a cycloalkyl which may be substituted with a halogen.

The structure

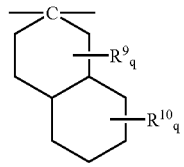

may be cited as an example, wherein $R^9$ and $R^{10}$ are identical or different, and, independently of each other, denote hydrogen, an alkyl containing 1 to 4 carbon atoms or a halogen, and q independent of each other represent an integer of 0 to 4.

It is also possible for up to two carbon units

which are contained in the cyclic structure

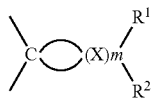

to be substituted by heteroatom units, for example —O—, —S—, —N—$R^1$— or —P—$R^1$—, wherein $R^1$ and $R^2$ are as described above.

The present invention further relates to the aforementioned compounds as flame retardants of thermoplastic compositions in particular of such compositions which contain polycarbonate, which may also be impact-modified, and to moldings which contain said thermoplastic compositions.

The flame retardants according to the invention make it possible to produce thermoplastic compositions or moldings which exhibit significantly improved dimensional stability under the effect of heat, good flowability and improved properties in relation to solvents (ESC behaviour).

The oligophosphates according to the invention may be used as flame retardants in thermoplastic compositions in amounts of 1 to 40% by weight, preferably 2 to 25% by weight, most preferably 3 to 20% by weight, with respect to the weight of the composition.

The oligophosphates according to the invention may be produced by the esterification of suitable compounds which contain two aromatic hydroxy functions with a phosphoric acid diphenyl ester halide in the presence of a base, for example. One particularly preferred oligophosphate is obtained, for example, by the esterification of trimethylcyclohexyl(TMC)-bisphenol with phosphoric acid diphenyl ester chloride in the presence of triethylamine, according to the following chemical equation:

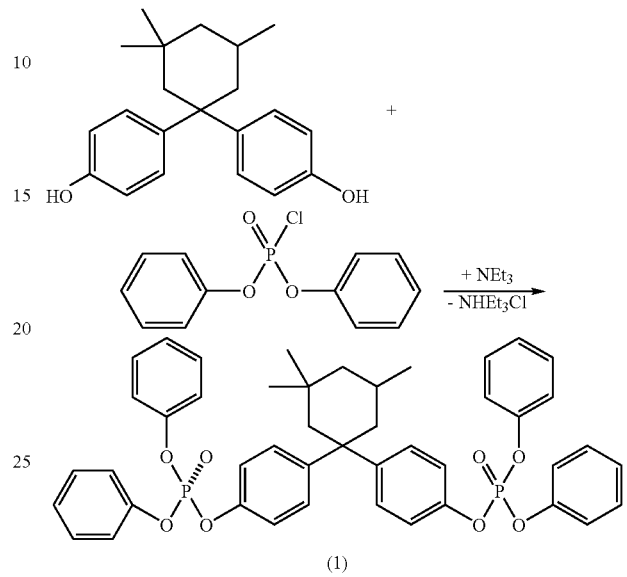

(1)

In addition to the flame retardants described above, the thermoplastic compositions according to the invention, particularly polycarbonate compositions, may also contain other thermoplastic polymers, particularly polyester carbonates, polyesters, ABS graft copolymers and vinyl (co)polymers.

These constituents, and other components which may be used in said compositions according to the invention, are described below by way of examples.

Component A

Aromatic polycarbonates and/or aromatic polyester carbonates which are suitable according to the invention for component A are known from the literature or may be produced by methods known from the literature (for the production of aromatic polycarbonates, see Schnell, "Chemistry and Physics of Polycarbonates", Interscience Publishers, 1964, and DE-AS 1 495 626, DE-A 2 232 877, DE-A 2 703 376, DE-A 2 714 544, DE-A 3 000 610 and DE-A 3 832 396, for example; for the production of aromatic polyester carbonates, see DE-A 3 077 934 for example).

Aromatic polycarbonates may be produced, for example, by the reaction of diphenols with carbonic acid halides, preferably phosgene, and/or with aromatic dicarboxylic acid dihalides, preferably benzene-dicarboxylic acid dihalides, by the phase boundary method, optionally with the use of chain terminators, for example monophenols, and optionally with the use of tri-functional branching agents or branching agents which exhibit a functionality greater than three, for example triphenols or tetraphenols.

The preferred diphenols for the production of aromatic polycarbonates and/or aromatic polyester carbonate are those of formula (I)

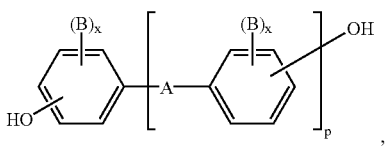

wherein
A is a single bond, a $C_1$ to $C_5$ alkylene, a $C_2$ to $C_5$ alkylidene, a $C_5$ to $C_6$ cycloalkylidene, —O—, —SO—, —CO—, —S—, —SO$_2$—, or a $C_6$ to $C_{12}$ arylene, on which other aromatic rings, which optionally contain heteroatoms, may be condensed,
or a radical of formulae (II) or (III)

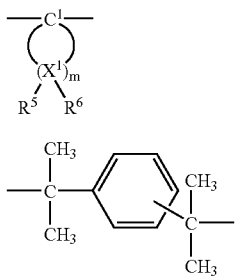

wherein
B in each case denotes a $C_1$ to $C_{12}$ alkyl, preferably methyl, or denotes a halogen, preferably chlorine and/or bromine,
x denotes numbers which, independently of each other, are 0, 1 or 2,
p denotes 1 or 0, and
$R^5$ and $R^6$ may be selected individually and independently of each other for each $X^1$, and denote hydrogen or a $C_1$ to $C_6$ alkyl, preferably hydrogen, methyl or ethyl,
$X^1$ denotes carbon, and
m is an integer from 4 to 7, preferably 4 or 5, with the proviso that at on least one atom $X^1$, $R^5$ and $R^6$ simultaneously denote an alkyl.

The preferred diphenols are hydroquinone, resorcinol, dihydroxydiphenols, bis(hydroxyphenyl)-$C_1$–$C_5$ alkanes, bis-(hydroxyphenyl)-$C_5$–$C_6$-cycloalkanes, bis(hydroxyphenyl) ethers, bis-(hydroxyphenyl) sulphoxides, bis-(hydroxyphenyl) ketones, bis-(hydroxyphenyl) sulphones and α,α-bis-(hydroxyphenyl)-diisopropyl-benzenes, as well as derivatives thereof which comprise brominated and/or chlorinated nuclei.

The diphenols which are particularly preferred are 4,4'-dihydroxydiphenyl, bisphenol A, 2,4-bis(4-hydroxyphenyl)-2-methylbutane, 1,1-bis-(4-hydroxyphenyl)-cyclohexane, 1,1-bis-(4-hydroxyphenyl)-3.3.5-trimethylcyclohexane, 4,4'-dihydroxy-diphenyl sulphide, 4,4'-dihydroxydiphenyl-sulphone, and di- and tetrabrominated or chlorinated derivatives thereof, such as 2,2-bis(3-chloro-4-hydroxyphenyl)-propane, 2,2-bis-(3,5-dichloro-4-hydroxyphenyl)-propane, or 2,2-bis-(3,5-dibromo-4-hydroxyphenyl)-propane. 2,2-bis-(4-hydroxyphenyl)-propane (bisphenol A) is particularly preferred.

These diphenols may be used individually or as any desired mixtures. These are known from the literature or may be obtained by methods known from the literature.

Examples of chain terminators which are suitable for the production of thermoplastic, aromatic polycarbonates include phenol, p-chlorophenol, p-tert.-butylphenol or 2,4,6-tribromophenol, and also include long chain alkylphenols such as 4-(1,3-tetramethyl-butyl)-phenol according to DE-A 2 842 005 or monoalkylphenol or dialkylphenols having a total of 8 to 20 carbon atoms in their alkyl substituents, such as 3,5-di-tert.-butyl phenol, p-iso-octylphenol, p-tert.-octylphenol, p-dodecylphenol, 2-(3,5-dimethylheptyl)-phenol and 4-(3,5-dimethylheptyl)-phenol. The amount of chain terminators used generally ranges between 0.5 mol % and 10 mol %, with respect to the molar sum of the diphenols used in each case.

These thermoplastic, aromatic polycarbonates have average (weight average) molecular weights (as measured by ultracentrifuge or of scattered light, for example) from 10,000 to 200,000. preferably from 15,000 to 80,000.

The thermoplastic, aromatic polycarbonates may be branched in the known manner, by the incorporation of 0.05 to 2.0 mol %, with respect to the sum of the diphenols used, of trifunctional compounds or compounds with a functionality greater than three, for example those comprising three or more phenolic groups.

Both homopolycarbonates and copolycarbonates are suitable. 1 to 25% by weight, preferably 2.5 to 25% by weight, with respect to the total amount of diphenols used, of polydiorganosiloxanes comprising hydroxyaryloxy terminal groups may also be used as component A for the production of copolycarbonates according to the invention. These are known (U.S. Pat. No. 3,419,634) and may be produced by methods known from the literature. The production of copolycarbonates which contain polydiorganosiloxanes is described in DE-A 3 334 782.

Apart from bisphenol A homopolycarbonates, preferred polycarbonates also include copolycarbonates of bisphenol A comprising up to 15 mol %, with respect to the sum of the moles of diphenols, of other diphenols cited as being preferred or most preferred, particularly 2,2-bis(3,5-dibromo-4-hydroxyphenyl)-propane.

The preferred aromatic dicarboxylic acid dihalides for the production of the aromatic polyester carbonates are preferably the diacid dichlorides of isophthalic acid, terephthalic acid, diphenylether-4,4'-dicarboxylic acid and naphthalene-2,6-dicarboxylic acid.

Mixtures of diacid dichlorides of isophthalic acid and terephthalic acid in a ratio between 1:20 and 20:1 are particularly preferred.

During the production of the polyester carbonates, a carbonic acid halide, preferably phosgene, is used in conjunction as a bifunctional derivative of an acid.

Apart from the aforementioned monophenols, suitable chain terminators for the production of the aromatic polyester carbonates include chlorocarbonic acid esters thereof, as well as acid chlorides of aromatic monocarboxylic acids, which may optionally be substituted by $C_1$ to $C_{22}$ alkyl groups or by halogen atoms, as well as aliphatic $C_2$ to $C_{22}$ monocarboxylic acid chlorides.

The amount of chain terminators preferably ranges from 0.1 to 10 mol %, which in the case of phenolic chain terminators is given with respect to moles of diphenol and in the case of monocarboxylic acid chloride chain terminators is given with respect to moles of dicarboxylic acid dichloride.

The aromatic polyester carbonates may also contain incorporated aromatic hydroxycarboxylic acids.

The aromatic polyester carbonates may either be linear or may be branched in the known manner (see DE-A 2 940 024 and DE-A 3 007 934 in this respect).

Examples of suitable branching agents include trifunctional carboxylic acid chlorides, or acid chlorides with a functionality greater than three, such as trimesic acid trichloride, cyanuric acid trichloride, 3,3'-,4,4'-benzophenone-tetracarboxylic acid tetrachloride, 1,4,5,8-napthalene-tetracarboxylic acid tetrachloride or pyromellitic acid tetrachloride, in amounts of 0.01 to 1.0 mol % (with respect to the dicarboxylic acid dichloride used) or tri- or multi-functional phenols such as phloroglucinol, 4,6-dimethyl-2,4,6-tri-(4-hydroxyphenyl)-heptene-2,4,4-dimethyl-2,4,6-tri-(4-hydroxy-phenyl)-heptane-1,3.5-tri-(4-hydroxyphenyl)-benzene, 1,1,1-tri-(4-hydroxyphenyl)-ethane-tri-(4-hydroxyphenyl)-phenylmethane, 2,2-bis[4,4-bis(4-hydroxyphenyl)-cyclo-hexyl]-propane, 2,4-bis(4-hydroxyphenyl-isopropyl)-phenol, tetra-(4-hydroxyphenyl)-methane, 2,6-bis(2-hydroxy-5-methyl-benzyl)-4-methyl-phenol, 2-(4-hydroxyphenyl)-2-(2,4-dihydroxyphenyl)-propane, tetra-(4-[4-hydroxy-phenyl-isopropyl]-phenoxy)-methane or 1,4-bis [4,4'-dihydroxytri-phenyl]-methyl]-benzene, in amounts of 0.01 to 1.0 mol % with respect to the diphenols used. Phenolic branching agents may be placed in the reaction vessel with diphenols, and acid chloride branching agents may be added together with the acid dichlorides.

In the thermoplastic, aromatic polyester carbonates, the proportion of carbonate structural units may be arbitrarily varied. The proportion of carbonate groups preferably ranges up to 100 mol %, particularly up to 80 mol %, most preferably up to 50 mol %, with respect to the sum of the ester groups and carbonate groups. Both the ester and the carbonate constituents of the aromatic polyester carbonates may exist in the form of blocks or may be randomly distributed in the condensation polymer.

The relative solution viscosities ($\eta_{rel}$) of the aromatic polycarbonates and polyester carbonates falls within the range from 1.18 to 1.4, preferably 1.20 to 1.32 (as measured on solutions of 0.5 g polycarbonate or polyester carbonate in 100 ml methylene chloride at 25° C.).

The thermoplastic, aromatic polycarbonates and polyester carbonates may be used on their own on in any admixture.

Component A is preferably contained in the compositions according to the invention in an amount of 5 to 95% by weight, more preferably 10 to 90% by weight, most preferably 20 to 80% by weight, with respect to the weight of the composition.

Component B

Component B comprises one or more graft polymers of

B.1 5 to 95, preferably 30 to 90% by weight, of at least one vinyl monomer on

B.2 95 to 5, preferably 70 to 10% by weight of one or more graft bases with glass transition temperatures <10° C., preferably <0° C., most preferably <−20° C.

Graft base B.2 generally has an mean particle size ($d_{50}$ value) of 0.05 to 10 μm, preferably 0.1 to 5 μm, most preferably 0.2 to 1 μm.

Monomers B.1 are preferably mixtures of

B.1.1 50 to 99 parts by weight of aromatic vinyl compounds and/or aromatic vinyl compounds comprising substituted nuclei (e.g. styrene, a-methylstyrene, p-methylstyrene, p-chlorostyrene) and/or $C_1$–$C_8$ alkyl esters of methacrylic acid (such as methyl methacrylate, ethyl methacrylate) and B.1.2 1 to 50 parts by weight of vinyl cyanides (unsaturated nitrites such as acrylonitrile and methacrylonitrile) and/or $C_1$–$C_8$ alkyl esters of methacrylic acid (such as methyl methacrylate, n-butyl acrylate, tert.-butyl acrylate) and/or derivatives (such as anhydrides and imides) of unsaturated carboxylic acids (for example maleic anhydride and N-phenyl-maleinimide).

The preferred monomers B.1.1 are at least one of the monomers styrene, α-methylstyrene and methyl methacrylate; the preferred monomers B.1.2 are at least one member selected from the group consisting of acrylonitrile, maleic anhydride and methyl methacrylate.

Monomers which are particularly preferred are styrene as B.1.1. and acrylonitrile as B.1.2.

Examples of suitable graft bases B.2 for graft polymer B include diene rubbers, EP(D)M rubbers, namely those based on ethylene/propylene, and optionally diene, acrylate, polyurethane, silicone chloroprene and ethylene/vinyl acetate rubbers.

The preferred graft bases B.2 are diene rubbers (e.g. those based on butadiene or isoprene) or mixtures of diene rubbers, or copolymers of diene rubbers, or mixtures thereof with other copolymerizable monomers (e.g. according to B.1.1 and B.1.2), with the proviso that the glass transition temperature of component B.2 is <10° C., preferably <0° C., most preferably <−10° C.

Pure polybutadiene rubber is particularly preferred.

Examples of particularly preferred polymers B include ABS polymers (emulsion, bulk and suspension ABS), such as those described in DE-A 2 035 390 (=U.S. Pat. No. 3,644,574) or in DE-A 2 248 242 (=GB-PS 1 409 275) and in Ullmanns Enzyklopädie der Technischen Chemie, Volume 19 (1980), page 280 et seq., for example. The gel content of graft base B.2 is at least 30% by weight, preferably at least 40% by weight (as measured in toluene).

Graft copolymers B are produced by radical polymerization, e.g. by emulsion, suspension, solution or bulk polymerisation, preferably by emulsion or bulk polymerisation.

Particularly suitable graft rubbers also include ABS polymers which are produced by redox initiation using an initiator system comprising an organic hydroperoxide and ascorbic acid according to U.S. Pat. No. 4,937,285.

Since, as is known, graft monomers are not necessarily grafted completely on to the graft base during graft polymerization, graft polymers B are also to be understood according to the invention as those products which are obtained by (co)polymerization of the graft monomers in the presence of the graft base and which are also present after work-up.

Suitable acrylate rubbers B.2 of polymers B are preferably polymers of acrylic acid alkyl esters, optionally with up to 40% by weight, with respect to B.2, of other polymerizable, ethylenically unsaturated monomers. The preferred polymerizable acrylic acid esters comprise $C_1$ to $C_8$ alkyl esters, for example methyl, ethyl, butyl, n-octyl- and 2-ethylhexyl esters; halogenoalkyl esters, preferably halogeno-$C_1$–$C_8$ alkyl esters such as chloromethyl acrylate, as well as mixtures of these monomers.

Monomers comprising more than one polymerizable double bond may be copolymerised to effect crosslinking. Preferred examples of crosslinking monomers include esters of unsaturated monocarboxylic acids comprising 3 to 8 C atoms and unsaturated monohydric alcohols comprising 3 to 12 C atoms, or saturated polyols comprising 2 to 4 OH groups and 2 to 20 C atoms, such as ethylene glycol dimethacrylate, allyl methacrylate; multiply-unsaturated heterocyclic compounds, such as trivinyl- and triallyl cyanurates; poly-functional vinyl compounds, such as di- and trivinylbenzenes; and also triallyl phosphate and diallyl phthalate.

The preferred crosslinking monomers are allyl methacrylate, ethylene glycol dimethacrylate, diallyl phthalate and heterocyclic compounds which contain at least three ethylenically unsaturated groups.

Crosslinking monomers which are particularly preferred are the cyclic monomers triallyl cyanurate, triallyl isocyanurate, triacryloyl hexahydro-s-triazine, and triallylbenzenes. The amount of crosslinked monomer is preferably 0.02 to 5, particularly 0.05 to 2% by weight, with respect to the graft base B.2.

When using cyclic crosslinking monomers comprising at least three ethylenically unsaturated groups, it is advantageous if the amount thereof is limited to less than 1% by weight of graft base B.2.

Examples of preferred "other" polymerizable, ethylenically unsaturated monomers which may optionally be employed apart from esters of acrylic acid for the production of graft base B.2, include acrylonitrile, styrene, α-methylstyrene, acrylamide, vinyl-($C_1$–$C_6$ alkyl) ethers, methyl methacrylate and butadiene. The preferred acrylate rubbers for use as graft base B.2 are emulsion polymers which have a gel content of at least 60% by weight.

Other suitable graft bases B.2 are silicone rubbers with graft-active sites, such as those described in DE-A 3 704 657, DE-A 3 704 655, DE-A 3 631 540 and DE-A 3 631 539.

The gel content of graft base B.2 is determined at 25° C. in a suitable solvent (M. Hoffmann, H. Krömer, R. Kuhn, Polymeranalytik I and 11, Georg Thieme-Verlag, Stuttgart 1977).

The mean particle size $d_{50}$ is the diameter above and below which 50% by weight of the particles occur. It may be determined by ultracentrifuge measurements (W. Scholtan, H. Lange, Kolloid, Z. und Z. Polymere 250 (1972), 782–1796).

Component B is preferably contained in the compositions according to the invention in an amount ranging from 1 to 60% by weight, more preferably from 1 to 40% by weight, most preferably from 2 to 30% by weight, with respect to the weight of the composition.

Component C

Component C comprises one or more thermoplastic vinyl (co)polymers C.1 and/or polyalkylene terephthalates C.2.

Polymers which are suitable as vinyl (co)polymers C.1 are polymers of at least one monomer from the group comprising aromatic vinyl compounds, vinyl cyanides (unsaturated nitriles), ($C_1$ to $C_8$) alkyl esters of (meth)acrylic acid, unsaturated carboxylic acids, and derivatives (such as anhydrides and imides) of unsaturated carboxylic acids. Polymers which are particularly suitable are (co)polymers of C.1.1 50 to 99, preferably 60 to 80 parts by weight of aromatic vinyl compounds and/or of aromatic vinyl compounds comprising substituted nuclei, such as styrene, α-methyl-styrene, p-methylstyrene, p-chlorostyrene, and/or ($C_1$ to $C_8$) alkyl esters of (meth)acrylic acid such as methyl methacrylate or ethyl methacrylate), and C.1.2 1 to 50, preferably 20 to 40 parts by weight of vinyl cyanides (unsaturated nitrites) such as acrylonitrile and methacrylonitrile, and/or ($C_1$ to $C_8$) alkyl esters of (meth) acrylic acid (such as methyl methacrylate, n-butyl acrylate, tert.-butyl acrylate) and/or unsaturated carboxylic acids (such as maleic acid) and/or derivatives (such as anhydrides and imides) of unsaturated carboxylic acids (for example maleic anhydride and N-phenyl-maleinimide).

(Co)polymers C.1 are resinous, thermoplastic and free from rubber.

A particularly preferred copolymer is that formed from styrene as C.1.1.and acrylonitrile as C.1.2.

(Co)polymers as defined by C.1 are known, and may be produced by radical polymerisation, particularly by emulsion, suspension, solution or bulk polymerisation. These (co)polymers preferably have average molecular weights $M_w$ (weight average molecular weights, as determined by light scattering or sedimentation) between 15,000 and 200,000.

The polyalkylene terephthalates of component C.2 are reaction products formed from aromatic dicarboxylic acids or reactive derivatives thereof, such as dimethyl esters or anhydrides, and aliphatic, cycloaliphatic or araliphatic diols, as well as mixtures of said reaction products.

The preferred polyalkylene terephthalates contain at least 80% by weight, preferably at least 90% by weight, with respect to the dicarboxylic acid component, of terephthalic acid radicals, and at least 80% by weight, preferably at least 90 mol %, with respect to the diol component, of ethylene glycol and/or 1,4-butanediol radicals.

Apart from terephthalic acid radicals, the preferred polyalkylene terephthalates may contain up to 20 mol %, preferably up to 10 mol %, of radicals of other aromatic or cycloaliphatic dicarboxylic acids comprising 8 to 14 C atoms, or of aliphatic dicarboxylic acids comprising 4 to 12 C atoms, such as radicals of phthalic acid, isophthalic acid, naphthalene-2,6-dicarboxylic acid, 4,4'-diphenyldicarboxylic acid, succinic acid, adipic acid, sebacic acid, azelaic acid, cyclohexane-diacetic acid.

Apart from ethylene glycol or 1,4-butanediol radicals, the preferred polyalkylene terephthalates may contain up to 20 mol %, preferably up to 10 mol %, of other aliphatic diols comprising 3 to 12 C atoms or of cycloaliphatic diols comprising 6 to 21 C atoms, e.g. radicals of 1,3-propanediol, 2-ethylpropanediol-1,3, neopentyl glycol, 1,5-pentanediol, 1,6-hexanediol, cyclohexane-dimethanol-1,4,3-ethylpentanediol-2,4,2-methylpentanediol-2,4,2,2,4-trimethylpentanediol-1,3,2-ethylhexane-diol-1,3,2,2-diethylpropanediol-1,3,2,5-hexanediol, 1,4-di-(β-hydroxyethoxy)-benzene, 2,2-bis-(4-hydroxycyclohexyl)-propane, 2,4-dihydroxy-1,1,3,3-tetramethyl-cyclobutane-2,2-bis-(4-β-hydroxyethoxyphenyl)-propane, and 2,2-bis-(4-hydroxypropoxyphenyl)-propane (DE-A 2 407 674, 2 407 776, 2 715 932).

The polyalkylene terephthalates may be branched by the incorporation of relatively small amounts of tri- or tetrahydric alcohols or tri- or tetrabasic carboxylic acids, e.g. according to DE-A 1 900 270 and U.S. Pat. No. 3,692,744. Examples of preferred branching agents include trimesic acid, trimellitic acid, trimethylolethane and -propane and pentaerythritol.

Polyalkylene terephthalates are particularly preferred which are produced solely from terephthalic acid and reactive derivatives thereof (e.g. dialkyl esters thereof) and ethylene glycol and/or 1,4-butanediol, as well as mixtures of said polyalkylene terephthalates.

Mixtures of polyalkylene terephthalates contain from 1 to 50% by weight, preferably from 1 to 30% by weight, of polyethylene terephthalate and from 50 to 99% by weight, preferably from 70 to 99% by weight, of polybutylene terephthalate.

The polyalkylene terephthalates which are preferably used generally have a limiting viscosity of 0.4 to 1.5 dl/g, preferably 0.5 to 1.2 dl/g, as measured in phenol/o-dichlorobenzene (in a 1:1 ratio by weight) at 25° C. in an Ubbelohde viscometer.

The polyalkylene terephthalates may be produced by known methods (e.g. Kunststoff-Handbuch, Volume VIII, page 695 et seq., Carl-Hanser-Verlag, Munich 1973).

Component C is preferably contained in the compositions according to the invention in an amount from 0 to 50% by weight, more preferably up to 30% by weight and most preferably up to 20% by weight, with respect to the weight of the composition.

Component D

Component D comprises very finely divided inorganic powders.

The very finely divided inorganic powders D which are used according to the invention preferably consist of one or more metals of Main Groups 1 to 5 or Subgroups 1 to 8 of the periodic table, preferably of Main Groups 2 to 5 or Subgroups 4 to 8, most preferably of Main Groups 3 to 5 or Subgroups 4 to 8, or are compounds of these metals with at least one element selected from oxygen, hydrogen, sulphur, phosphorus, boron, carbon, nitrogen or silicon.

Examples of preferred compounds include oxides, hydroxides, hydrated oxides, sulphates, sulphites, sulphides, carbonates, carbides, nitrates, nitrites, nitrides, borates, silicates, phosphates, hydrides, phosphites or phosphonates.

The very finely divided inorganic powders preferably consist of oxides, phosphates or hydroxides, most preferably of $TiO_2$, $SiO_2$, $SnO_2$, $ZnO$, $ZnS$, boehmite, $ZrO_2$, $Al_2O_3$, aluminium phosphate or iron oxides, or of TiN, WC, AlO(OH), $5B_2O_3$, $NaSO_4$, vanadium oxides, zinc borate, silicates such as Al silicate, Mg silicate, and one-, two- and three-dimensional silicates. Mixtures and doped compounds may also be used.

Moreover, these nano-scale particles may be surface-modified with organic molecules in order to improve the compatibility thereof with polymers. Hydrophobic or hydrophilic surfaces may be produced in this manner.

Hydrated aluminas such as boehmite, or $TiO_2$, are particularly preferred.

The average particle diameters of the nano-particles are less than or equal to 1000 nm, preferably less than or equal to 500 nm, particularly 1 to 100 nm.

The terms "particle size" and "particle diameter" always denote the mean particle diameter $d_{50}$ as determined by ultracentrifuge measurements according to W. Scholtan et al., Kolloid-Z. und Z. Polymere 250 (1972), pages 782–796.

The inorganic powders are incorporated in the thermoplastic molding composition in amounts from 0 to 40, preferably from 0 to 25, most preferably from 0.1 to 15% by weight, with respect to the thermoplastic material.

The inorganic compounds may be present as powders, pastes, sols, dispersions or suspensions. Powders may be obtained by precipitation from dispersions, sols or suspensions.

The powders may be incorporated in the thermoplastic molding compositions by customary methods, for example by the direct kneading or extrusion of molding compositions and the very finely divided inorganic powders.

Component E

The flame retardants according to the invention may be used in combination with what are termed anti-dripping agents, which reduce the tendency of the material to drip as burning droplets in the event of fire. Examples of suitable anti-dripping agents include compounds from the classes of substances comprising fluorinated polyolefines, silicones and aramid fibres. These may also be used in the compositions according to the invention. Fluorinated polyolefines are preferably used as anti-dripping agents.

Fluorinated polyolefines are known, and are described in the EP-A 0 640 655 for example. They are sold by DuPont under the Trademark Teflon® 30N.

These fluorinated polyolefines may be used either in pure form or in the form of a coagulated mixture comprising emulsions of fluorinated polyolefines with emulsions of the graft polymers (component B) or with an emulsion of a copolymer, preferably a styrene/acrylonitrile-based copolymer, wherein the fluorinated polyolefine is mixed as an emulsion with an emulsion of the graft polymer or of the copolymer and is subsequently coagulated.

Furthermore, fluorinated polyolefines may be used as a preliminary compound with the graft polymer (component B) or with a copolymer, preferably a styrene/acrylonitrile-based copolymer. The fluorinated polyolefines are mixed as powders with a powder or with granules of the graft polymer or copolymer and are compounded in the melt, generally at temperatures from 200 to 330° C. in customary processing units such as internal kneaders, extruders or twin-shaft continuous screw devices.

The fluorinated polyolefines may also be used in the form of a master batch which is produced by the emulsion polymerisation of at least one monoethylenically unsaturated monomer in the presence of an aqueous dispersion of the fluorinated polyolefine. The preferred monomer components are styrene, acrylonitrile and mixtures thereof. After precipitation by acid and subsequent drying, the polymer is used as a free-flowing powder.

The coagulates, preliminary compounds or master batches usually have solids contents of fluorinated polyolefines from 5 to 95% by weight, preferably 7 to 60% by weight. The compositions may contain fluorinated polyolefines in amounts from 0 to 4% by weight, preferably up to 2% by weight, and most preferably from 0.1 to 0.5% by weight, with respect to the weight of the composition.

F. Other Additives

The molding compositions according to the invention may also contain at least one of the customary additives such as internal lubrimayts and demolding agents, for example pentaerythritol tetrastearate, nucleating agents, anti-static agents, stabilisers, fillers and reinforcing agents such as glass or carbon fibres, talc, wollastonite, mica, kaolin, $CaCO_3$ and glass flakes, as well as colorants and pigments.

The molding compositions according to the invention may contain up to 35% by weight, with respect to the molding composition, of a further flame retardant which optionally has a synergistic effect. Examples of further flame retardants include compounds which contain phosphorus, such as organophosphates, organophosphonates, phosphonatamines or phosphazenes, organic halogen compounds such as decabromobisphenyl ether, tetrabromobisphenol, inorganic halogen compounds such as ammonium bromide, nitrogen compounds such as melamine and melamine-formaldehyde resins, inorganic hydroxide compounds such as Mg or Al hydroxide, inorganic compounds such as antimony oxide, barium metaborate, hydroxoantimonate, zirconium oxide, zirconium hydroxide, molybdenum oxide, ammonium molybdate, zinc borate, ammonium borate, barium metaborate, talc, silicates, aluminosilicates, silica and tinoxide, as well as siloxane compounds.

Apart from the very finely divided inorganic powders cited as component D, talc is also preferably used as a synergistic flame retardant (FR). The term "talc" is to be understood to mean a naturally occurring or synthetically produced talc which is optionally calcined.

The composition of pure talc corresponds to the formula 3MgO.4SiO$_2$.H$_2$O and it thus has an MgO content of 31.9% by weight, an SiO$_2$ content of 63.4% by weight and a content of chemically bound water of 4.8% by weight. It is a silicate with a layer structure.

Naturally occurring talc materials generally do not have the aforementioned ideal composition, since they are contaminated due to the partial replacement of the magnesium by other elements, by the partial replacement of silicon by aluminium for example, and/or by growths of other minerals such as dolomite, magnesite or chlorite.

Particularly high purity types of talc are preferably used, which are characterised by an MgO content of 28 to 35% by weight, preferably 30 to 33% by weight, most preferably 30.5 to 32% by weight, and an SiO$_2$ content of 55 to 65% by weight, preferably 58 to 64% by weight, most preferably 60 to 62.5% by weight. The most preferred types of talc are further characterised by an Al$_2$O$_3$ content less than 5% by weight, most preferably less than 1% by weight, particularly less than 0.7% by weight.

The talc according to the invention is advantageously used in the form of finely ground types which are optionally surface-modified (silanised), with a largest mean particle size d$_{50}$ of <20 µm, preferably <10 µm, more preferably <5 µm, most preferably <2.5 µm.

The molding compositions according to the invention are produced by mixing the respective constituents in the known manner and by compounding and extruding them in the melt at temperatures from 200° C. to 300° C. in customary processing units such as internal kneaders, extruders and twin-shaft continuous screw devices.

Mixing of the individual constituents may be effected in the known manner, either successively or simultaneously, and may be conducted either at about 20° C. (room temperature) or at an elevated temperature.

The molding compositions according to the invention may be used for the production of moldings of any type, which may be produced by injection molding, extrusion or blow-molding methods. Another form of processing is the production of moldings by thermoforming them from previously produced sheet or film.

Example of these moldings are sheeting, sections, housing parts of all types, e.g. for domestic appliances such as juice presses, coffee machines, mixers; for office equipment such as monitors, printers, copiers; sheeting, tubes, electrical installation conduits, windows, doors and other sections for the construction industry (interior fittings and exterior applications), as well as electrical and electronic parts such as switches, plugs and sockets.

In particular, the molding compositions according to the invention may also be used for the production of the following moldings or molded components, for example:

Interior and exterior components for railway vehicles, ships, aircraft, buses and other motor vehicles, exterior bodywork parts in the automobile industry, housing for electrical appliances which contain miniature transformers, housings for information processing and transmission devices, housings and coverings for medical equipment, massage equipment and housings therefor, toy vehicles for children, sheet-like wall elements, housings for safety devices, thermally insulated transport containers, apparatuses for housing or transporting small animals, moldings for sanitary and bath fittings, covering grilles for ventilation openings, moldings for garden buildings and tool sheds or houses for garden equipment.

The following examples explain the invention in more detail.

EXAMPLES

Example 1

Examples 1 to 4 Illustrate the Production of Flame Retardants According to the Invention.

A compound containing phosphorus according to the invention was obtained by the following reaction:

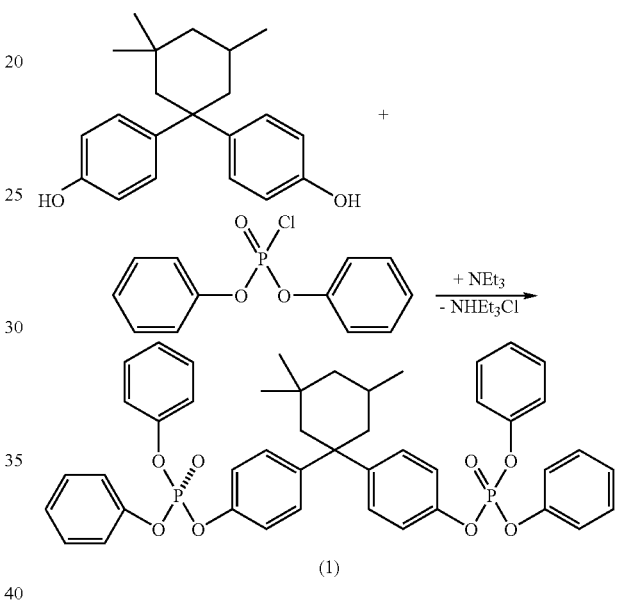

1.1 kg 3,3,5-trimethylcyclohexyl(TMC)-bisphenol and 1.0 l triethylamine were introduced at 5° C. in 2.0 l tetrahydrofuran. 2.0 kg phosphoric acid diphenyl ester chloride were steadily added drop-wise over a period of 2.5 hours at 5 to 9° C. The batch was subsequently stirred for 18 hours at room temperature. The salts were filtered off under suction and washed with tert.-butyl methyl ether (3×400 ml). The combined organic phases were washed with 1 N sodium hydroxide solution (3×500 ml) and water (500 ml), dried over magnesium sulphate and concentrated by evaporation. The residue was dissolved in dichloromethane (1000 ml) and was once again extracted with 1 N sodium hydroxide solution (3×1000 ml), and was then dried over magnesium sulphate and concentrated by evaporation. 2.0 kg of the white solid target compound (1) were thus obtained in a purity of 99%, corresponding to 73% theoretical. The following analysis results were obtained for this substance:

| | |
|---|---|
| HPLC-MS: | purity > 99% of area |
| MS (ES$^+$): | 775 (24) [MH$^+$], 792 (100) [M$^+$ + H$_2$O] |
| P: elemental analysis: | 7.9% (theoretical value 8.0%) |
| DIN acid number: | 0.25 |
| Melting point: | 89° C. |

Example 2

A compound containing phosphorus according to the invention was obtained by the following reaction:

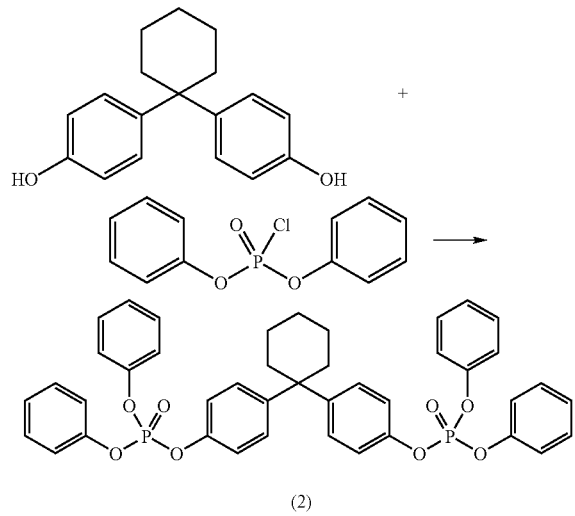

(2)

0.5 kg cyclohexyl-1,1-bis(4-phenol) and 0.40 kg triethylamine were introduced at 0° C. into 1.5 l tetrahydrofuran. 1.05 kg phosphoric acid diphenyl ester were steadily added drop-wise over a period of 3.5 hours at −5 to 12° C. The batch was subsequently stirred for 18 hours at room temperature. The salts were filtered off under suction and washed with tert.-butyl methyl ether (4×1000 ml). The combined organic phases were washed with 1 N sodium hydroxide solution (5×500 ml) and water (500 ml), dried over magnesium sulphate and concentrated by evaporation. 1.25 kg of compound (2) were thus obtained in a purity of 100%, corresponding to 91% theoretical. The following analysis results were obtained for this substance:

| | |
|---|---|
| HPLC-MS: | purity: 100% of area |
| MS (ES$^+$): | 733 (100) [MH$^+$] |
| P: elemental analysis: | 8.0% (theoretical value 8.4%) |
| DIN acid number: | 0.76 |

Example 3

A compound containing phosphorus according to the invention was obtained by the following reaction:

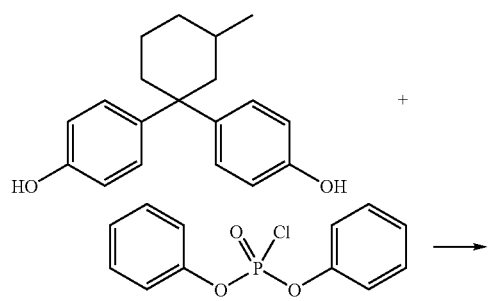

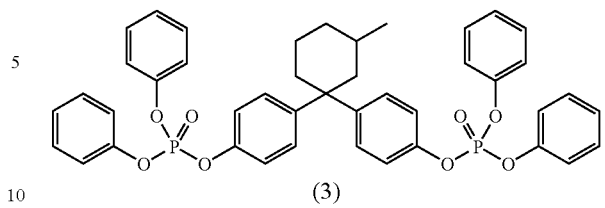

(3)

0.5 kg 3-methylcyclohexyl-1,1-bis(4-phenol) and 0.38 kg triethylamine were introduced at 0C into 1.5 l tetrahydrofuran. 1.00 kg phosphoric acid diphenyl ester was steadily added drop-wise over a period of 4.3 hours at −8 to 13° C. The batch was subsequently stirred for 18 hours at room temperature. The salts were filtered off under suction and washed with THF (1500 ml) and tert.-butyl methyl ether (2×1000 ml). The combined organic phases were washed with 1 N sodium hydroxide solution (5×500 ml) and water (500 ml), dried over magnesium sulphate and concentrated by evaporation. 1.27 kg of compound (3) were thus obtained in a purity of 100%, corresponding to 96% theoretical. The following analysis results were obtained for this substance:

| | |
|---|---|
| HPLC-MS: | purity: 100% of area |
| MS (ES$^+$): | 747 (100) [MH$^+$] |
| P: elemental analysis: | 8.0% (theoretical value 8.3%) |
| DIN acid number: | 0.54 |

Example 4

A compound containing phosphorus according to the invention was obtained by the following reaction:

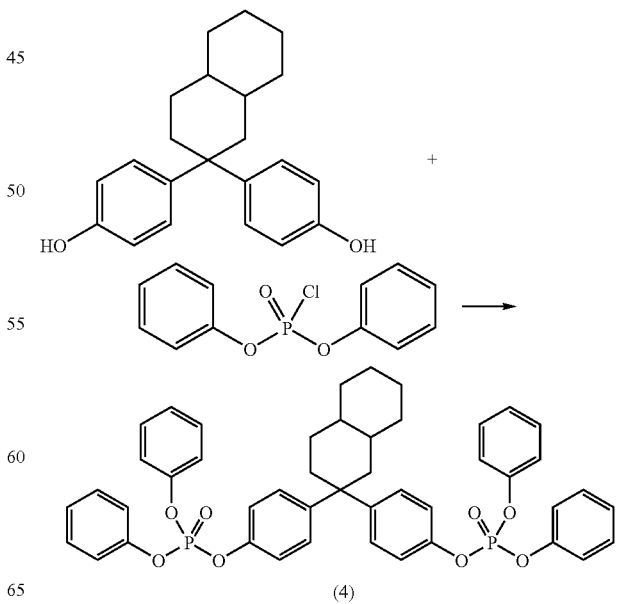

(4)

0.15 kg decahydronaphthyl-2,2-bis(4-phenol) and 0.10 kg triethylamine were introduced at 0° C. into 1.0 l tetrahydrofuran. 0.26 kg phosphoric acid diphenyl ester was steadily added drop-wise over a period of 2.5 hours at −2 to 18° C. The batch was subsequently stirred for 18 hours at room temperature. The salts were filtered off under suction and washed with tert.-butyl methyl ether (3×700 ml). The combined organic phases were washed with 1 N sodium hydroxide solution (5×500 ml) and water (500 ml), dried over magnesium sulphate and concentrated by evaporation. 0.36 kg of compound (4) was thus obtained in a purity of 67% (balance: triphenyl phosphate), corresponding to 66% theoretical. The following analysis results were obtained for this substance:

| | |
|---|---|
| HPLC-MS: | purity: 67% of area |
| MS (ES+): | 787 (100) [MH+] |
| P: elemental analysis: | 7.9% (theoretical value 7.9%) |
| DIN acid number: | 0.27 |

General Methods of Analysis

HPLC—HPLC measurements on the substance from Example 1 were performed using an Agilent 1100 chromatograph with an HTS PAL injector supplied by CTC Analytics. Separations were made on an Inertsil ODS-3 stationary phase (length: 250 mm, inside diameter 2.1 mm, particle size 5 μm) at 40° C. and at a flow rate of 0.2 ml/min. The liquid phase consisted of a gradient of A (water+0.01% formic acid) and B (acetonitrile+0.05% formic acid) comprising 5% B at 0 minutes and a gradient of up to 100% B at 20 minutes, and then 100% B at 30 minutes. UV measurements were made at λ=214 nm.

HPLC measurements on the substances from Examples 2 to 4 were performed using an Agilent 1100 chromatograph with an HTS PAL injector supplied by CTC Analytics. Separations were made on a Nucleosil $C_{18}$ stationary phase (length: 50 mm, inside diameter 2 mm, particle size 3 μm) at 35° C. and at a flow rate of 0.5 ml/min. The liquid phase consisted of a gradient of A (water+0.05% formic acid) and B (acetonitrile+0.05% formic acid) comprising 5% B at 0 minutes and a gradient of up to 100% B at 12 minutes, and then 100% B at 15 minutes. UV measurements were made at λ=210 to 500 nm.

MS—Mass spectra of the substance from Example 1 were measured using a Finnigan TSQ 700 spectrophotometer with (+) electrospray in the m/z range from 200 to 1500.

Mass spectra of the substances from Examples 2 to 4 were measured using a Waters ZMD 2000 spectrophotometer with (+) electrospray in the m/z range from 110 to 1500.

Acid number—The acid number was determined at least twice according to DIN 53 402. The average value is given. About 1 g sample was accurately weighed (to 0.001 g) into the titration vessel and was dissolved in 50 ml of a mixture comprising 2 parts by volume toluene and 1 part by volume ethanol (95% by volume). For difficultly soluble substances, it was possible to increase the amount of solvent by up to three times, or up to 25 ml acetone was added. After adding 2 to 3 drops of phenolphthalein solution at room temperature, the solution was rapidly titrated with alcoholic KOH (prepared by dissolving 5.611 g KOH in ethanol (95% by volume) until the red coloration which was formed remained for at least 10 seconds (consumption a). During the titration it had to be ensured that no precipitates formed. The latter could be re-dissolved if necessary by adding a little solvent. A blank test was performed in the same manner but without any sample (consumption b).

The acid number in mg KOH/g was calculated from the following equation:

$$\text{For } c(\text{KOH}) = 0.1 \text{ mol}/l : \text{acid number} = \frac{(a-b) \times 5.61}{E}$$

where a consumption in ml of KOH solution during the titration of the sample b consumption in ml of KOH solution in blank test E amount weighed in (g)

5.61 factor for converting ml KOH solution, c(KOH)=0.1 mol/l, into mg KOH

Production and Testing of Molding Compositions According to the Invention and of Comparison Molding Compositions.

Thermoplastic polycarbonate molding compositions 1 to 5 (according to the invention) and V1 and V2 (comparison) were produced using the oligophosphates from Examples 1 to 4 and using known oligo-phosphates. The compositions of the molding compositions are given in Table 1.

The components listed in Table 1, which are briefly explained below, were compounded in a 3 liter internal kneader or in a ZSK-25 device at 240° C. The moldings were produced in an Arburg 270 E injection molding machine at 240°.

Component A.1

A linear polycarbonate based on bisphenol A with a relative solution viscosity of 1.24, as measured in $CH_2Cl_2$ as the solvent at 25° C. and at a concentration of 0.5 g/100 ml.

Component A.2

A linear polycarbonate based on bisphenol A with a relative solution viscosity of 1.25, as measured in $CH_2Cl_2$ as the solvent at 25° C. and at a concentration of 0.5 g/100 ml.

Component B.1

A graft polymer comprising 40 parts by weight of a copolymer of styrene and acrylonitrile in a ratio of 73:27 on 60 parts by weight of particulate crosslinked polybutadiene rubber (mean particle diameter $d_{50}$=0.3 μm), produced by emulsion polymerisation.

Component B.2

A graft polymer comprising 84 parts by weight of a copolymer of styrene and acrylonitrile in a ratio of 73:27 on 16 parts by weight of particulate crosslinked polybutadiene rubber produced by bulk polymerisation.

Component C

A styrene/acrylonitrile copolymer with a ratio by weight of styrene to acrylonitrile of 72:28 and a limiting viscosity of 0.55 dl/g (as measured in dimethylformamide at 20° C.).

Component D.1

An oligophosphate based on bisphenol A

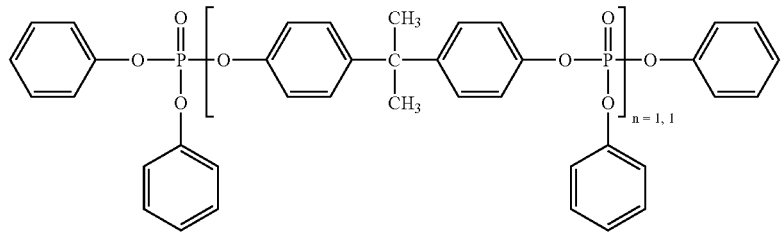

Component D.2

The TMC-bisphenol diphosphate from Example 1.

Component D.3

The methylcyclohexyl-bisphenol diphosphate from Example 3.

Component D.4

The cyclohexyl-bisphenol diphosphate from Example 2.

Component E.1

Talc: Naintsch® A3 (Naintsch Mineralwerke GmbH, Graz, Austria) with an average particle diameter of 1.2 µm.

Component E.2

Pural® 200, a nano-scale aluminium hydroxide [AlO(OH)], average particle size approximately 50 nm (supplied by Condea, Hamburg, Germany)

Component F.1

A tetrafluorethylene polymer as a coagulated mixture comprising an SAN graft polymer emulsion of the aforementioned component B in water and a tetrafluorethylene polymer emulsion in water. The ratio by weight of graft polymer B to tetrafluorethylene polymer E in the mixture was 90% by weight to 10% by weight. The tetrafluorethylene polymer emulsion had a solids content of 60% by weight and an average particle diameter between 0.05 and 0.5 µm. The SAN graft polymer emulsion had a solids content of 34% by weight and an average latex particle diameter of $d_{50}$=0.3 µm.

The emulsion of tetrafluorethylene polymer (Teflon® 30 N) was mixed with the emulsion of SAN graft polymer B and was stabilised with 1.8% by weight, with respect to polymer solids, of phenolic anti-oxidants. The mixture was coagulated at 85 to 95° C. with a solution of $MgSO_4$ (Epsom salts) and acetic acid at pH 4 to 5, filtered, and washed until it was practically free from electrolytes; it was then freed from the bulk of the water by centrifugation and thereafter was dried at 100° C. to form a powder.

Component F.2

Blendex® 449: A PTFE preparation supplied by of General Electric Plastics, comprising 50% by weight PTFE and 50% by weight of an SAN copolymer.

Component G.1

A phosphite stabiliser

Component G.2

Pentaerythritol tetrastearate (PETS) as a demolding agent

Testing of the Molding Compositions According to the Invention

The Vicat B and HDT/A resistances to thermal deformation was determined according to DIN 53 460 (ISO 306) and ISO 75, respectively, on bars of dimensions 80 mm×10 mm×4 mm.

The notched bar impact value $a_k$ was determined according to ISO 180/1 A.

The behaviour in fire of the samples was measured according to UL 94 V on bars of thickness 1.6 and 3.2 mm.

The UL 94 V-Test was performed as follows:

Samples of substances were molded into bars of dimensions 127 mm×12.7 mm×1.6 (3.2) mm. The bars were mounted vertically so that the underside of the specimen was situated 305 mm above a strip of wadding material. Each test bar was ignited individually by means of two successive ignition operations of 10 seconds duration, the burning properties after each ignition were observed, and thereafter the sample was assessed. A Bunsen burner with a blue flame 10 mm (3.8 inches) high was used to ignite the samples. The gas supplied to the burner was natural gas with a calorific value of $3.73 \times 10^4$ kJ/m³ (1000 BTU per cubic foot).

The UL 94 V-O Classification covers the properties of materials described below, which were tested according to the UL 94 V regulations. The molding compositions in this class contained no samples which burned for longer than 10 seconds after each application of the test flame; they did not exhibit a total after-burn time of more than 50 seconds after two applications of the flame to each set of specimens comprising five bars; they contained no specimens which burned away completely down to the holding clamp fixed to the upper end of the specimen; they comprised no specimens which ignited the wadding under the specimen due to burning drops or particles; they also contained no specimens which glowed for longer than 30 seconds after the test flame was removed.

Other UL 94 Classifications designate specimens which are less flame-retardant or less self-extinguishing, because they give off flaming droplets or particles and/or exhibit longer total after-burn times. These classifications are denoted by UL 94 V-1 and V-2 N.R. denotes "non-resistant", and is the classification of specimens for which repeated after-burn times of ≧30 seconds were observed on the first and/or second application of the flame, or for which the total after-burn time exceeded 250 seconds on all 10 applications of the flame.

The stress cracking behaviour (ESC behaviour) was tested on bars of dimensions 80 mm×10 mm×4 mm. A mixture of toluene (60% by volume) and isopropanol (40% by volume) was used as the test medium. The specimens were pre-stretched by means of a template in the form of a circular arc (pre-stretching in percent) and were stored in the test medium at room temperature. The stress cracking behaviour was assessed via the formation of cracks or breaks in the test medium as a function of pre-stretching.

The melt viscosity was determined at 260° C. and at a shear rate of 1000 sec$^{-1}$ according to DIN 54811. The MVR (melt volume rate) was determined according to ISO 1133 at 240° C. using a plunger load of 5 kg.

The properties of the compositions according to the invention or of moldings obtained therefrom are listed in Table 1.

TABLE 1

| Molding composition/components | V1 | 1 | V2 | 2 | 3 | 4 | 5 |
|---|---|---|---|---|---|---|---|
| A1 | 65.3 | 63.9 | — | — | — | 64.7 | 64.4 |
| A2 | — | — | 70.6 | 70.6 | 69.4 | — | — |
| B1 | 7.0 | 6.8 | 3.7 | 3.7 | 3.6 | 6.9 | 6.9 |
| B2 | — | — | 11.0 | 11.0 | 10.8 | — | — |
| C | 6.0 | 5.9 | — | — | — | 5.9 | 5.9 |
| D1 | 14.6 | — | 12.5 | — | — | — | — |
| D2 | — | 16.4 | — | 12.5 | 14.0 | — | — |
| D3 | — | — | — | — | — | — | 15.7 |
| D4 | — | — | — | — | — | 15.4 | — |
| E1 | 2.0 | 2.0 | — | — | — | 2.0 | 2.0 |
| E2 | — | — | 0.8 | 0.8 | 0.8 | — | — |
| F1 | 4.6 | 4.5 | — | — | — | 4.6 | 4.6 |
| F2 | — | — | 0.9 | 0.9 | 0.9 | — | — |
| G1 | 0.1 | 0.1 | 0.1 | 0.1 | 0.1 | 0.1 | 0.1 |
| G2 | 0.4 | 0.4 | 0.4 | 0.4 | 0.4 | 0.4 | 0.4 |
| Compounding: | | | | | | | |
| ZSK 25 | x | x | — | — | — | — | — |
| Internal kneader | — | — | x | x | x | x | x |
| Properties: | | | | | | | |
| HDT/A[° C.] | 80 | 85 | 83 | 89 | 87 | — | — |
| Vicat B 120 [° C.] | 96 | 104 | 102 | 110 | 108 | 97 | 99 |
| ESC behaviour: break at ex [%] | 2.2 | 2.4 | 2.2 | 2.4 | 2.4 | 2.0 | 2.0 |
| $a_k$ [kJ/m$^2$] | 20 | 20 | 42 | 45 | 45 | 17 | 18 |
| MVR (240° C./5 kg) [ml/10 min] | 22 | 23 | 30 | 26 | 27 | 27 | 49 |
| Melt viscosity (260° C/100s$^{-1}$) [Pa.s] | 143 | 139 | 154 | 168 | 161 | 113 | 104 |
| UL 94 V at 3.2 mm (Total after-burn time) [sec]) | V-0 (7) | V-0 (6) | V-0 (17) | V-0 (13) | V-0 (13) | V-0 (14) | V-0 (5) |
| UL 94 V at 1.6 mm (Total after-burn time) [sec] | V-0 (21) | V-0 (22) | — | — | — | V-0 (24) | — |

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A compound conforming to

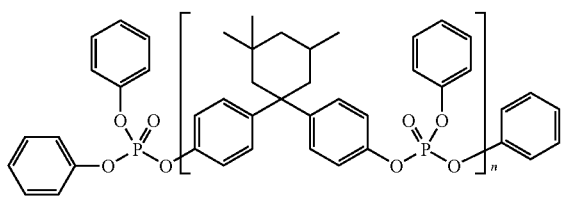

wherein n denotes an integer of 1 to 30.

2. A thermoplastic composition containing at least one thermoplastic resin and the compound according to claim 1.

3. The thermoplastic composition according to claim 2 wherein the thermoplastic resin is a member selected from the group consisting of polycarbonate, polyester carbonate, polyphenylene oxide, polyester, polyamide, polyester amide, vinyl (co)polymer and acrylic/butadiene/styrene (ABS) copolymer.

4. The thermoplastic composition according to claim 2 comprising a polycarbonate, wherein, with respect to the weight of the composition, said composition contains up to 50% by weight of a graft polymer comprising 5 to 95% by weight of that polymer of at least one vinyl monomer grafted on 95 to 5% by weight of at least one rubber as graft base having a glass transition temperature lower than about 10° C.

5. The thermoplastic composition according to claim 4 wherein the graft base is a member selected from the group consisting of diene-, EP(D)M-, acrylate- and silicone rubber.

6. The thermoplastic composition according to claim 4 wherein graft polymer is an emulsion- or bulk-polymerized ABS or mixtures thereof.

7. The thermoplastic composition according to claim 2 which further contains a fluorinated polyolefin.

8. The thermoplastic composition according to claim 2 which further contains a nano-scale inorganic material or talc.

9. A molded article comprising the composition of claim 2.

* * * * *